United States Patent [19]
Keltner

[11] Patent Number: 4,604,987
[45] Date of Patent: Aug. 12, 1986

[54] HEATED STADIUM CUSHION

[76] Inventor: Heidi Keltner, 1905 Calle de Vega, Las Vegas, Nev. 89102

[21] Appl. No.: 784,553

[22] Filed: Oct. 4, 1985

[51] Int. Cl.$^4$ ............................................. A61F 7/00
[52] U.S. Cl. .................................. 126/204; 126/206; 5/462; 5/466
[58] Field of Search ...................... 126/204, 206, 263; 5/462, 466, 470; 297/180, 219

[56] References Cited

U.S. PATENT DOCUMENTS

| | | | |
|---|---|---|---|
| 2,429,973 | 11/1947 | Alexander | 126/204 |
| 2,675,798 | 4/1954 | Rosmarin | 126/204 |
| 4,241,721 | 12/1980 | Holly | 126/204 |

Primary Examiner—Randall L. Green
Attorney, Agent, or Firm—Seiler, Quirk & Tratos

[57] ABSTRACT

A heated stadium cushion has a pad having a pocket adapted to contain an air-activated chemical heating packet. A second pocket contains weather-resistant clothing, such as a poncho. In another embodiment a slipcover is provided for enclosing a conventional seat cushion, the slipcover having an enclosed pocket for the heating element.

8 Claims, 8 Drawing Figures

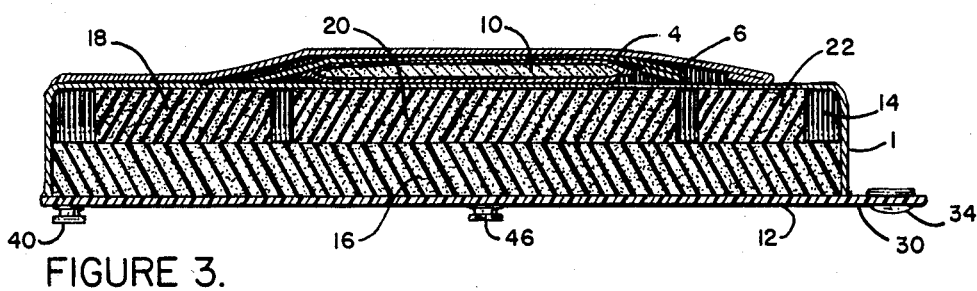
FIGURE 3.
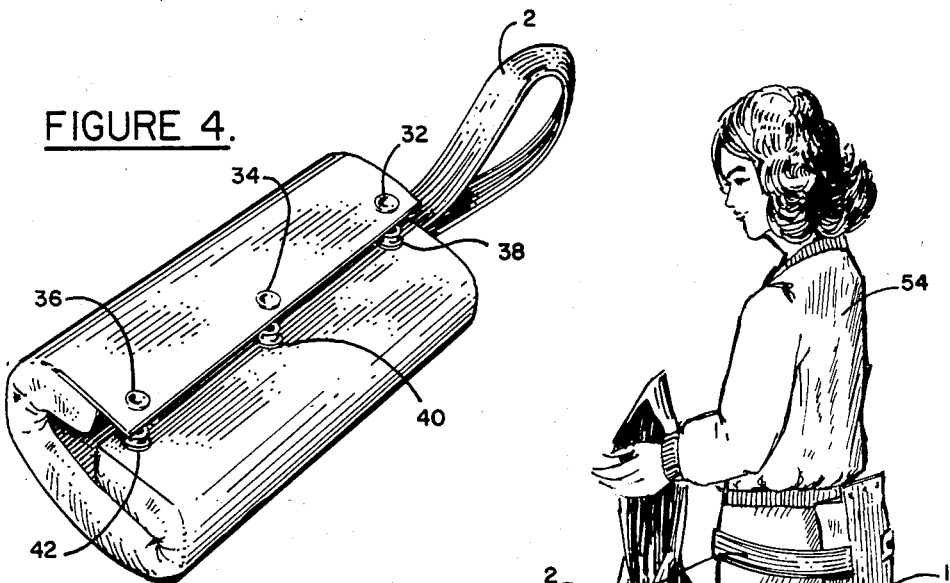
FIGURE 4.
FIGURE 5.
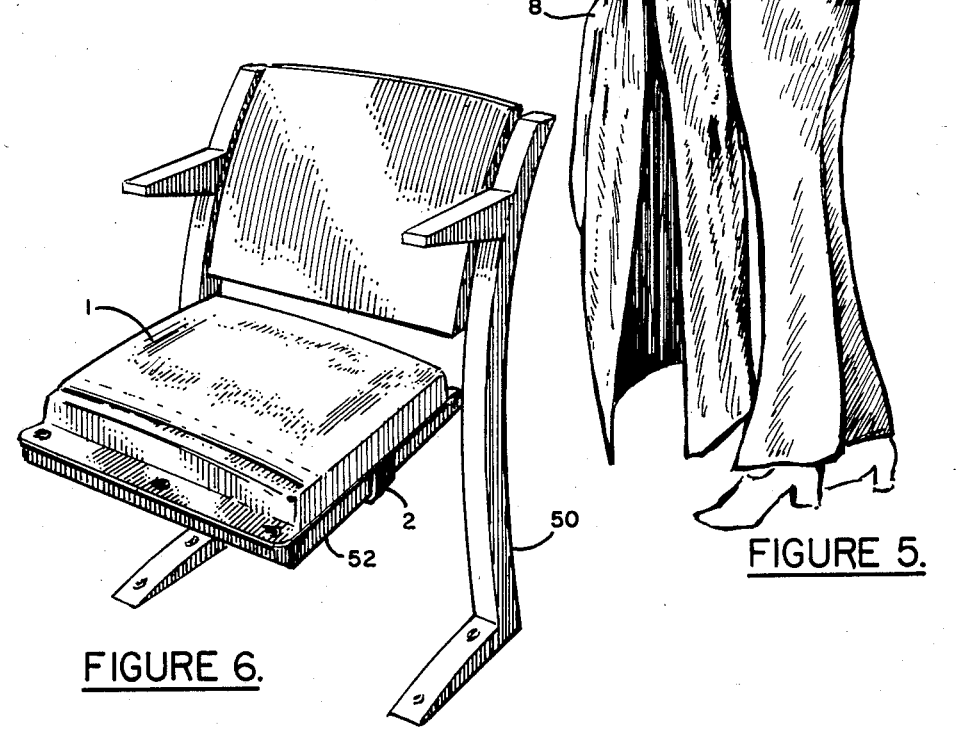
FIGURE 6.

HEATED STADIUM CUSHION

BACKGROUND OF THE INVENTION

This invention relates to a cushion used by a spectator at stadium events having a self-contained heating element. More particularly, it relates to a stadium cushion having a first pocket which encloses air-activated chemical heating means, and a second pocket that holds weather-resistant clothing, such as a poncho. In another embodiment, the invention relates to a slipcover for a conventional stadium cushion having a pocket which encloses a heating element.

It is very common for spectators at stadium events to carry portable cushions into the stadium to provide an additional degree of comfort when seated for long periods of time. These cushions generally consist of relatively thin foam pads encased in plastic, and frequently have a molded handle which enables easy portability. These devices are relatively inexpensive, and are frequently sold or leased at a stadium by schools or booster clubs to raise funds.

Cold weather is a common problem for many spectators of stadium events. Since the season for high school, college, and professional football extends into the winter, it is not uncommon for spectators to be subjected to extremely cold temperatures during these events. While it is always possible for the spectators to dress warmly, and to carry blankets, cushions, and rain gear, the ability of a spectator to remain comfortable has generally almost always depended on his ability to capture and retain his own body heat. In other words, there has been no practical capability of having externally generated heat to assist in keeping a spectator warm.

The present invention provides a spectator seat cushion which contains a conventional chemical heating element which is located in a pocket and is replaceable, and which also includes weather-resistant clothing, such as a poncho, in another pocket. In an alternate embodiment, the invention contemplates a slipcover for use with a conventional stadium cushion, with a chemical heating element contained within a pocket on the slipcover. In this embodiment, a user simply places the slipcover of the invention over an existing stadium cushion, and inserts a heating element into the pocket on the slipcover.

In the past, there have been a number of methods of heating cushions. For example, in Tilles, U.S. Pat. No. 3,259,925, a multi-layered cushion is disclosed which is said to reflect body heat, thereby warming the cushion. Various types of electrically heated cushions are also known. An electrically-heated cushion/heating pad is disclosed in U.S. Pat. No. 1,881,198. Electrically heated mattresses and cushions are shown in Yuen et al, U.S. Pat. No. 3,772,717, and Kidwell, U.S. Pat. No. 2,162,021. A combination poncho/cushion having a battery-energized heating element is disclosed in Browder, U.S. Pat. No. 4,035,606. The heating element is an electrical resistance wire which extends throughout the cushion. Unfortunately, the battery size necessary to generate sufficient heat for this apparatus makes it somewhat cumbersome.

It is also well known to generate heat by means of various exothermic chemical reactions. Various handwarmers, which may be used e.g., for skiing and the like, may contain iron powder which oxidizes on exposure to air, liberating heat. An infant mattress which includes a hot pack for chemically-generating heat is disclosed in Williams, U.S. Pat. No. 3,854,156; various chemicals are disclosed as operative but generally include at least one which is retained within a rupturable bag. A more complex electrochemical system is disclosed in Peterson et al, U.S. Pat. No. 4,095,583. A constant temperature pad having various chemicals which are injected into the pad in a liquid form is disclosed in Watson et al, U.S. Pat. No. 3,951,127. Devices using liquids have the disadvantage, when used in applicant's environment, of being somewhat difficult to use and also of being susceptible to leaks.

The present invention contemplates the use of finely divided solid chemical heat-generating compositions, which are pre-packaged in small packets which may be from 2" square to 4" square. Packets may be of a type such as those disclosed in O'Neal et al, U.S. Pat. No. 1,613,120, or Simmons, U.S. Pat. No. 1,953,513. These devices generally consist of powdered solids which include elemental iron along with various other salts and a small amount of water, and are prepackaged and sealed into an air-free environment.

The device of the invention consists of a simple, inexpensive cushion having pockets for retaining a solid chemical heating element and weather-resistant clothing. Alternatively, a slipcover for existing conventional cushions has the same functional elements. This enables a spectator to maintain comfort throughout the course of a stadium event, regardless of the exterior temperature.

Accordingly, it is an object of this invention to provide a seat cushion for use in stadium events which generates heat, thereby keeping the user warm throughout the event. It is another object of the invention to provide a heated cushion which is easily portable, and which can be rolled up into a relatively small package for easy portability. It is yet another object of the invention to provide a slipcover with retention means for enclosing a chemical heating element for use on conventional stadium cushions. These and other objects of the invention are achieved by the devices of the invention, which are described in more detail hereinafter.

BRIEF SUMMARY OF THE INVENTION

A heated stadium cushion comprises a foam pad which is enclosed in a unitary flexible casing having a pair of pockets, one for retaining a conventional chemical heating element which generates heat upon exposure to air, and one for retaining weather-resistant clothing, such as a poncho. The device also contains a strap for carrying the cushion or for fastening it to a chair or to the body of the user, and also carries interengaging fastening means for folding the cushion into a compact package for transport. Also contemplated is a slipcover for use on a conventional stadium cushion having pockets for the chemical heating element and the weather-resistant clothing.

BRIEF DESCRIPTION OF THE DRAWINGS

The invention is best understood with respect to the drawings, in which:

FIG. 3 is a side section view of the cushion with a chemical heating element in place in the interior pocket;

FIG. 4 is a perspective view of the cushion rolled up for carrying;

FIG. 5 shows the cushion strapped to the body of the user;

FIG. 6 shows the cushion strapped to a stadium seat;

DESCRIPTION OF PREFERRED EMBODIMENTS

Figure 1:
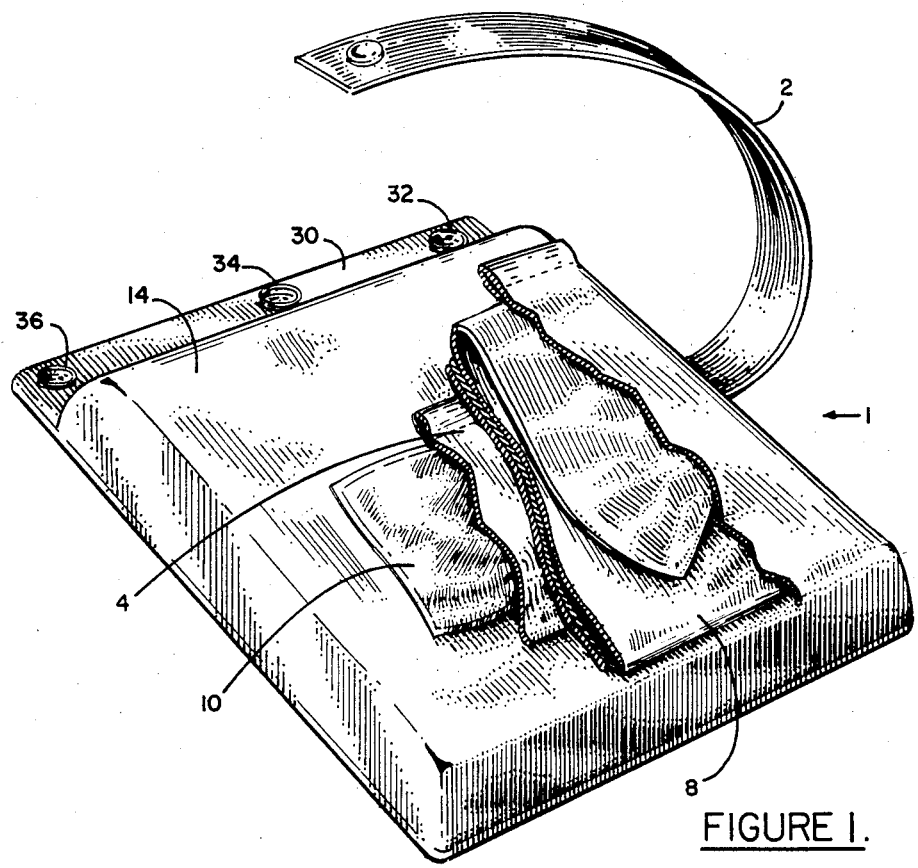
FIG. 1 is a perspective view of a cushion of the invention, with the pockets partially cut away.

Referring first to FIG. 1, cushion 1 having carrying strap 2 having one end thereof sewn to the side of the cushion and having the other end freely extending, has a pair of pockets mounted thereon and formed by means of an interior panel 4 and an exterior panel 6. The interior panel is sewn along three sides to the exterior covering 14 of the cushion, thereby forming a pocket into which chemical heating element 10 may be slideably inserted. The interior pocket is contained within the exterior pocket formed by panel 6, which has three sides integrally attached to the exterior cushion casing and which has an opening 9 for receiving weather-resistant clothing, such as a cap or a poncho 8, as depicted in FIG. 1.

Chemical heating element 10 may be any device which generates substantial heat by means of a chemical reaction, but preferably comprises a solid granular material which generates an exothermic reaction on exposure to air. Typically, such a device comprises finely divided elemental iron and certain salts packaged in an air-permeable enclosure. An example is the hand warmer marketed commercially as HandiHeat ® hand-warmer, which consists of iron powder, water, salt, and activated charcoal, and which is manufactured by Hakugen Co., Ltd., of Tokyo, Japan. The granular materials are packaged in an air-permeable packet which is enclosed in an air-tight plastic envelope. When the envelope is removed and the packet is exposed to air, the oxidation of the iron produces a steady heat at about 130°–150° F. for 5–7 hours. If the packet is replaced in the air-tight envelope during its useful life, the reaction stops and will restart on re-exposure to air.

The interior construction of the cushion is best shown in FIG. 3. The cushion is formed from a generally flat, rectangular piece of flexible foam 12, and a second layer of three pieces of foam 18, 20, and 22 which mount on top of the bottom foam layer. The use of three separate panels of foam on the top layer enables the pillow to be folded easily along the separations between the panels into a configuration shown in FIG. 4. If sufficiently thin foam is used for the cushion, the segmented foam design is not necessary, and the entire interior of the cushion may be fabricated from a single piece of flexible foam. Any soft, synthetic material may be used for the interior of the pillow, but a plastic foam such as polyurethane, polyethylene, or polystyrene, is preferred. The casing 14 for the cushion may also be formed from any sheet plastic material, such as vinyl or polyethylene, or may be a woven fabric. The casing portion 14 is flexible, and is unitary, i.e., surrounds the entirety of the interior foam. The casing is preferably water-impermeable and air impermeable to prevent water from entering the foam and to reflect heat outwardly. The pocket members 4 and 6 must be fabricated from an air-permeable material in order to provide a source of air to the heat element; fabric, or water-resistant nylon, are examples of acceptable materials. In the embodiment shown in FIG. 3, the pockets and casing are water-resistant nylon fabric, and the rear panel 12 is vinyl.

The rear portion of the casing 14 consists of a flat panel 12 having a flange portion 30 which extends out beyond the edge of the cushion. The flange bears three equally spaced female snap fasteners 32, 34, and 36 which face upwardly on the flange. These snap fasteners are positioned to engage male snap fastener members 38, 40, and 42 which extend downwardly from the rear casing panel 12 when the cushion is folded for carrying as shown in FIG. 4.

Figure 2:
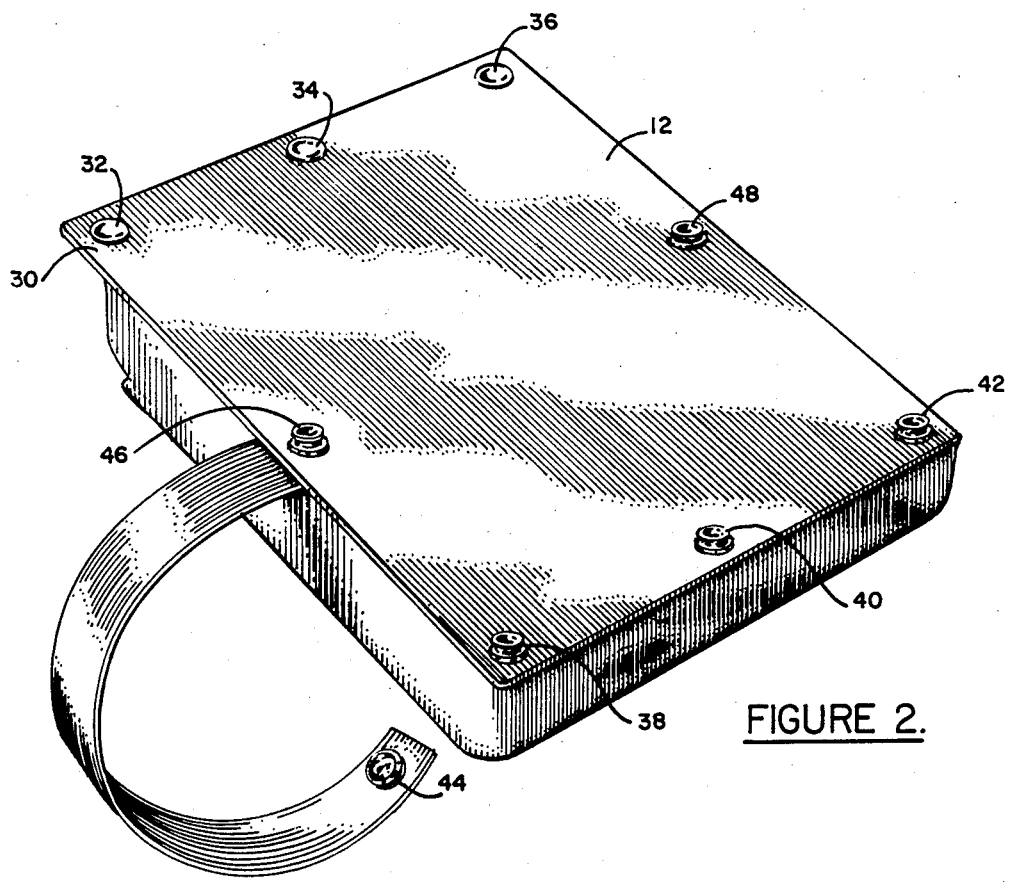
FIG. 2 is a bottom perspective view of the cushion.

The free end of strap 2 also has a female snap fastening member 44 located near the end thereof. This member is adapted to mate with either male coupling members 46 or 48, which are located along opposing longitudinal edges of the rear panel of the casing as shown in FIG. 2. When coupling elements 44 and 46 are mated, the strap retains a looped configuration as shown in FIG. 4, and can be used as a handle for carrying the cushion. Alternatively, the strap may be used to fasten the cushion to a person 54 as shown in FIG. 5, or to the seat portion 52 of stadium seat 50, as shown in FIG. 6.

While the various fastening means shown in FIGS. 1–6 have been shown to be conventional snap couplers, any interengaging fastening means may be used to attach the various components of the cushion of the invention. Particularly preferred interengaging fastening means are Velcro fasteners which are widely used commercially and which consist of patches of hooks and loops which interlock when pressed together but which may be easily pulled apart. The Velcro fasteners have all of the advantages of an adhesive, but selectively adhere to other Velcro members and do not adhere to other surfaces. Velcro fasteners for a cushion of the invention is shown in FIG. 7.

Figure 7:
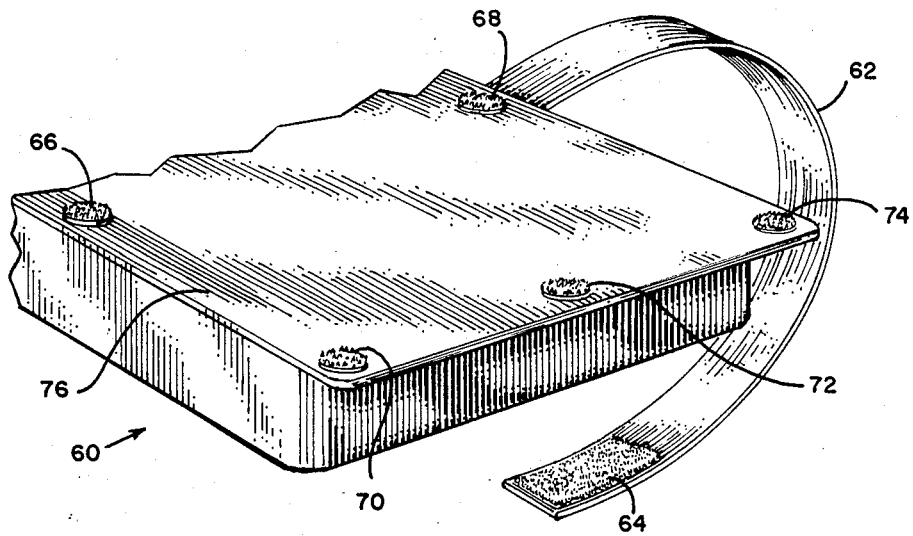
FIG. 7 shows a version of the cushion of the invention which uses Velcro fasteners.

Referring to FIG. 7, heated cushion 60 has a carrying strap 62 having a patch of Velcro 64 carrying a plurality of hook fastening means. Mating patches of Velcro 66, 68, 70, 72, and 74 are mounted adhesively on the rear panel 76 of the cushion in locations similar to the snap fasteners shown in FIG. 2. The hook portions and loop portions of the Velcro interengaging fastening means attach by pressure in well-known fashion.

Figure 8:
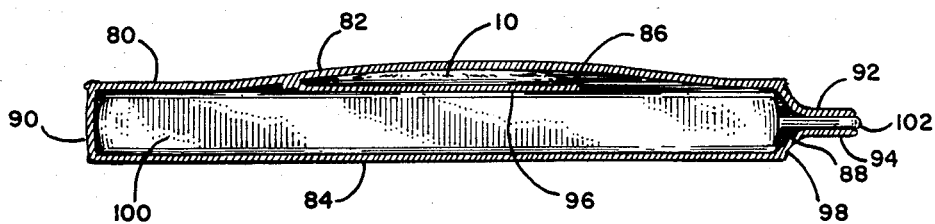
FIG. 8 is a view showing a slipcover of the invention mounted over a conventional stadium cushion.

FIG. 8 shows another embodiment of the invention which comprises a generally flexible slipcover which is used to enclose a conventional stadium cushion. In FIG. 8, the cushion consists of a vinyl-covered foamed plastic pad 100 having a molded plastic handle 102 having an opening therein (not shown) for gripping the handle. A slipcover 80 is shown in place around the cushion and comprises top panel 82, bottom panel 84, and an interior pocket-forming panel 96 for holding chemical heating element 10. The pocket is of size and shape similar to the pocket shown in FIG. 1, and may vary widely in size depending on the size of the heating element used in the cushion. The slip cover has a handle portion formed by opposing flanges 92 and 94 which orient adjacent the cushion handle 102 and have corresponding openings (not shown) corresponding to the openings in the cushion handle. The flanges 92 and 94 form an opening 88 at the top of the slipcover into which the cushion can be inserted. The cushion has an end panel 90 and a pair of front panel portions 98 which form the balance of the slip cover. To use the device, the slipcover is placed over the conventional cushion, and the heating element is inserted through the opening 88 into the interior pocket of the slipcover. Because the slipcover is made from an air-permeable material, such as fabric or water-resistant nylon, having air permeability, adequate air will enter the heating element to actuate the required chemical reaction.

While the invention has been described with respect to preferred embodiments thereof, modifications thereto will be readily apparent to those skilled in the art. Accordingly, the invention should not be considered limited by the foregoing description, but rather should be restricted only by the following claims.

I claim:

1. In combination, a heated cushion device comprising a foam pad enclosed in a unitary flexible casing, a first pocket attached to an exterior portion of the casing adapted to enclose a heating element, a second pocket attached to the casing adapted to enclose at least one article of weather-resistant clothing, handle means attached to the casing for carrying the device, said first pocket is located interior of said second pocket and an air-activated chemical heating element enclosed within said first pocket.

2. The combination of claim 1 wherein the strap is an elongate elastic member having one end thereof permanently attached to the casing, and interengaging fastening means fixed to another end of said strap means.

3. The combination of claim 2 also comprising interengaging fastening means mounted on the casing to enable the other end of the strap means to be removably affixed to the casing, thereby forming a loop functional as a carrying handle.

4. The combination of claim 1 also comprising at least one article of weather-resistant clothing mounted in said second pocket.

5. The combination of claim 1 wherein the cushion device comprises third interengaging fastening means mounted proximate to an edge of the cushion device, and fourth interengaging fastening means adapted to engage with said third interengaging fastening means mounted on an opposing edge of the cushion device, said third and fourth interengaging fastening means being oriented on said cushion device such that the device may be rolled into a generally cylindrical position, and may be retained in said position by attachment of said respective interengaging fastening means.

6. In combination, a cushion comprising a flexible foam pad enclosed within a flexible casing having generally flat front and back panels, and a removable slipcover comprising a flexible, air permeable material adapted to slideably receive the cushion and to retain generally the same size and shape as said cushion, said slipcover also having front and back panels, and pocket means mounted on a panel of the slipcover, and an air-activated chemical heating pad slideably engaged in said pocket.

7. The combination of claim 6 wherein the pocket means is located interior of the slipcover.

8. The combination of claim 6 wherein the chemical heating element comprises a granular mixture of iron, salt, and water.

* * * * *